(12) United States Patent
Quisenberry

(10) Patent No.: US 10,149,927 B2
(45) Date of Patent: Dec. 11, 2018

(54) METHOD AND SYSTEM FOR THERAPEUTIC USE OF ULTRA-VIOLET LIGHT

(71) Applicant: ThermoTek, Inc., Flower Mound, TX (US)

(72) Inventor: Tony Quisenberry, Highland Village, TX (US)

(73) Assignee: ThermoTek, Inc., Flower Mound, TX (US)

( * ) Notice: Subject to any disclaimer, the term of this patent is extended or adjusted under 35 U.S.C. 154(b) by 354 days.

(21) Appl. No.: 13/796,139

(22) Filed: Mar. 12, 2013

(65) Prior Publication Data

US 2013/0281947 A1   Oct. 24, 2013

Related U.S. Application Data

(60) Provisional application No. 61/637,601, filed on Apr. 24, 2012.

(51) Int. Cl.
*A61M 1/00* (2006.01)
*A61N 5/06* (2006.01)
(Continued)

(52) U.S. Cl.
CPC ......... *A61M 1/0023* (2013.01); *A61N 5/0613* (2013.01); *A61N 5/0616* (2013.01); *A61M 1/0088* (2013.01); *A61M 2205/053* (2013.01); *A61N 2005/005* (2013.01); *A61N 2005/0644* (2013.01); *A61N 2005/0649* (2013.01); *A61N 2005/0652* (2013.01); *A61N 2005/0661* (2013.01)

(58) Field of Classification Search
CPC .......... A61M 1/00; A61M 5/178; A61M 5/00; A61M 35/00; A61F 13/00; A61F 13/02
See application file for complete search history.

(56) References Cited

U.S. PATENT DOCUMENTS

| | | |
|---|---|---|
| 773,828 A | 11/1904 | Titus |
| 2,110,022 A | 3/1938 | Kliesrath |

(Continued)

FOREIGN PATENT DOCUMENTS

| | | |
|---|---|---|
| CH | 670 541 | 6/1989 |
| DE | 35 22 127 | 1/1987 |

(Continued)

OTHER PUBLICATIONS

American Heritage Dictionary of the English Language. 2011.*
(Continued)

*Primary Examiner* — Tatyana Zalukaeva
*Assistant Examiner* — Ilya Treyger
(74) *Attorney, Agent, or Firm* — Winstead PC

(57) ABSTRACT

In one aspect, the present invention relates to a wound care system. The wound care system includes a power unit and a processor coupled to the power unit. An ultra-violet light-emitting diode array is electrically coupled to the processor. A thermoelectric element is thermally exposed to the ultra-violet light-emitting diode array. A probe is optically coupled to the ultra-violet light-emitting diode array. The thermoelectric element cools the ultra-violet light emitting diode array thereby optimizing the ultra-violet light emitting diode array.

18 Claims, 13 Drawing Sheets

(51) Int. Cl.
   *A61M 5/178* (2006.01)
   *A61M 5/00* (2006.01)
   *A61M 35/00* (2006.01)
   *A61F 13/00* (2006.01)
   *A61F 13/02* (2006.01)
   *A61N 5/00* (2006.01)

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,179,106 A | 4/1965 | Meredith |
| 3,345,641 A | 10/1967 | Jennings |
| 3,367,319 A | 2/1968 | Carter, Jr. |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,419,988 A | 12/1983 | Mummert |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,523,594 A | 6/1985 | Kuznetz |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,795,435 A | 1/1989 | Steer |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Home et al. |
| 4,926,881 A | 5/1990 | Ichinomiya et al. |
| 4,962,761 A | 10/1990 | Golden |
| 4,979,375 A | 10/1990 | Nathans et al. |
| 4,969,881 A | 11/1990 | Viesturs |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,315,994 A | 5/1994 | Guibert et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,636,643 A | 6/1997 | Argenta et al. |
| D380,874 S | 7/1997 | Caswell |
| 5,645,081 A | 7/1997 | Argenta et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,669,872 A | 9/1997 | Fox |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |

(56) References Cited

U.S. PATENT DOCUMENTS

| | | |
|---|---|---|
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,865,841 A | 2/1999 | Kolen et al. |
| 5,871,526 A | 2/1999 | Gibbs et al. |
| 5,890,371 A | 4/1999 | Rajasubramanian et al. |
| 5,897,581 A | 4/1999 | Fronda et al. |
| 5,901,037 A | 5/1999 | Hamilton et al. |
| 5,923,533 A | 7/1999 | Olson |
| 5,947,914 A | 9/1999 | Augustine |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,156,059 A | 12/2000 | Olofsson |
| 6,176,869 B1 | 1/2001 | Mason et al. |
| 6,178,562 B1 | 1/2001 | Elkins |
| 6,186,977 B1 | 2/2001 | Andrews et al. |
| 6,231,532 B1 | 5/2001 | Watson et al. |
| 6,235,049 B1 | 5/2001 | Nazerian |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,312,453 B1 | 11/2001 | Stefanile et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |
| 6,462,949 B1 | 10/2002 | Parish, IV et al. |
| 6,468,237 B1 | 10/2002 | Lina |
| 6,508,831 B1 | 1/2003 | Kushnir |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| 6,551,347 B1 | 4/2003 | Elkins |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| D515,218 S | 2/2006 | McGuire et al. |
| 7,004,915 B2 | 2/2006 | Boynton et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| 7,195,624 B2 | 3/2007 | Lockwood et al. |
| 7,198,046 B1 | 4/2007 | Argenta et al. |
| 7,216,651 B2 | 5/2007 | Argenta et al. |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| 7,524,286 B2 | 4/2009 | Johnson |
| 7,532,953 B2 | 5/2009 | Vogel |
| 7,553,306 B1 | 6/2009 | Hunt et al. |
| D595,620 S | 7/2009 | Kingsbury |
| D601,707 S | 10/2009 | Chouiller |
| 7,608,066 B2 | 10/2009 | Vogel |
| 7,618,382 B2 | 11/2009 | Vogel et al. |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| 7,763,000 B2 | 7/2010 | Risk, Jr. et al. |
| 7,799,004 B2 | 9/2010 | Tumey |
| 7,804,686 B2 | 9/2010 | Parish et al. |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| 7,811,269 B2 | 10/2010 | Boynton et al. |
| D627,896 S | 11/2010 | Matsuo et al. |
| D628,300 S | 11/2010 | Caden |
| 7,837,673 B2 | 11/2010 | Vogel |
| D630,759 S | 1/2011 | Matsuo et al. |
| 7,867,206 B2 | 1/2011 | Lockwood et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,864 B2 | 3/2011 | Lockwood et al. |
| 7,896,910 B2 | 3/2011 | Schirrmacher et al. |
| 7,909,861 B2 | 3/2011 | Balachandran et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 7,959,588 B1 | 6/2011 | Wolpa |
| 8,007,491 B2 | 8/2011 | Pinto et al. |
| D649,648 S | 11/2011 | Cavalieri et al. |
| 8,052,630 B2 | 11/2011 | Kloecker et al. |
| 8,084,663 B2 | 12/2011 | Watson, Jr. |

(56) References Cited

U.S. PATENT DOCUMENTS

| | | |
|---|---|---|
| 8,088,113 B2 | 1/2012 | Scherson et al. |
| 8,100,956 B2 | 1/2012 | Quisenberry et al. |
| 8,109,981 B2 * | 2/2012 | Gertner et al. ............... 607/88 |
| D655,420 S | 3/2012 | Bowles |
| D655,821 S | 3/2012 | Matsuo |
| 8,128,672 B2 | 3/2012 | Quisenberry et al. |
| 8,142,486 B2 | 3/2012 | Quisenberry et al. |
| D657,063 S | 4/2012 | Chiang |
| 8,157,792 B2 * | 4/2012 | Dolliver et al. ............. 604/543 |
| D660,438 S | 5/2012 | Kennedy et al. |
| D660,439 S | 5/2012 | Chen et al. |
| D662,212 S | 6/2012 | Quisenberry |
| D662,213 S | 6/2012 | Quisenberry |
| D662,214 S | 6/2012 | Quisenberry |
| 8,202,262 B2 | 6/2012 | Lina et al. |
| D663,850 S | 7/2012 | Joseph |
| D664,260 S | 7/2012 | Quisenberry |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,240,885 B2 * | 8/2012 | Miller .................... F21S 8/038 362/294 |
| 8,248,798 B2 | 8/2012 | Parish et al. |
| D679,023 S | 3/2013 | Quisenberry |
| 8,425,580 B2 | 4/2013 | Quisenberry et al. |
| D683,042 S | 5/2013 | Quisenberry |
| 8,444,581 B1 | 5/2013 | Maxon-Maldonado et al. |
| 8,485,995 B1 | 7/2013 | Maxon-Maldonado |
| 8,529,613 B2 | 9/2013 | Radziunas et al. |
| 8,569,566 B2 | 10/2013 | Blott et al. |
| 8,574,278 B2 | 11/2013 | Quisenberry |
| 8,632,576 B2 | 1/2014 | Quisenberry |
| 8,753,300 B2 | 6/2014 | Deshpande |
| 8,753,383 B2 | 6/2014 | Parish et al. |
| 8,758,419 B1 | 6/2014 | Quisenberry et al. |
| 8,772,567 B2 * | 7/2014 | Eckstein ................ A61L 15/26 602/46 |
| 8,778,005 B2 | 7/2014 | Parish et al. |
| 8,827,935 B2 | 9/2014 | Maxon-Maldonado |
| 8,834,393 B2 | 9/2014 | Maxon-Maldonado et al. |
| 8,940,034 B2 | 1/2015 | Quisenberry |
| 9,101,463 B2 | 8/2015 | Stormby |
| 9,114,055 B2 | 8/2015 | Edelman et al. |
| 9,119,705 B2 | 9/2015 | Parish et al. |
| 9,132,057 B2 | 9/2015 | Wilford et al. |
| 9,180,041 B2 | 11/2015 | Parish et al. |
| 9,192,539 B2 | 11/2015 | Parish et al. |
| 9,669,233 B2 | 6/2017 | Quisenberry et al. |
| 2001/0018604 A1 | 8/2001 | Elkins |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0125649 A1 | 7/2003 | McIntosh et al. |
| 2003/0127215 A1 | 7/2003 | Parish, IV et al. |
| 2003/0135252 A1 | 7/2003 | MacHold et al. |
| 2003/0139255 A1 | 7/2003 | Lina |
| 2003/0163183 A1 | 8/2003 | Carson |
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0176805 A1 | 9/2004 | Whelan et al. |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0080465 A1 | 4/2005 | Zelickson et al. |
| 2005/0126578 A1 | 6/2005 | Garrison et al. |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0187500 A1 | 8/2005 | Perry et al. |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0116620 A1 | 6/2006 | Oyaski |
| 2006/0167531 A1 | 7/2006 | Gertner et al. |
| 2006/0241549 A1 | 10/2006 | Sunnen |
| 2006/0253089 A1 | 11/2006 | Lin |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 * | 3/2008 | Quisenberry et al. .......... 607/88 |
| 2008/0082029 A1 | 4/2008 | Diana |
| 2008/0103397 A1 | 5/2008 | Barak |
| 2008/0103422 A1 | 5/2008 | Perry et al. |
| 2008/0125775 A1 | 5/2008 | Morris |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |
| 2008/0319362 A1 | 12/2008 | Joseph |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2009/0237264 A1 | 9/2009 | Bobey |
| 2009/0254159 A1 | 10/2009 | Stormby |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 * | 6/2010 | Bernstein ............... A61K 31/00 424/447 |
| 2010/0179469 A1 | 7/2010 | Hammond et al. |
| 2010/0186436 A1 | 7/2010 | Stormby |
| 2010/0210982 A1 | 8/2010 | Balachandran et al. |
| 2010/0249679 A1 | 9/2010 | Perry et al. |
| 2010/0249680 A1 | 9/2010 | Davis |
| 2011/0009785 A1 | 1/2011 | Meyer et al. |
| 2011/0034861 A1 | 2/2011 | Schaefer |
| 2011/0037002 A1 | 2/2011 | Johnson et al. |
| 2011/0071447 A1 | 3/2011 | Liu et al. |
| 2011/0082401 A1 | 4/2011 | Iker et al. |
| 2011/0087142 A1 | 4/2011 | Ravikumar et al. |
| 2011/0275983 A1 | 11/2011 | Quisenberry et al. |
| 2011/0282269 A1 | 11/2011 | Quisenberry et al. |
| 2012/0041526 A1 | 2/2012 | Stormby |
| 2012/0130457 A1 | 5/2012 | Gammons et al. |
| 2012/0259266 A1 | 10/2012 | Quisenberry |
| 2013/0030331 A1 | 1/2013 | Quisenberry et al. |

(56) References Cited

U.S. PATENT DOCUMENTS

| | | |
|---|---|---|
| 2013/0191437 A1 | 7/2013 | Itoh |
| 2013/0216627 A1 | 8/2013 | Galbraith et al. |
| 2013/0245508 A1 | 9/2013 | Maxon-Maldonado |
| 2013/0245519 A1 | 9/2013 | Edelman et al. |
| 2013/0253383 A1 | 9/2013 | Maxon-Maldonado |
| 2013/0261512 A1 | 10/2013 | Maxon-Maldonado et al. |
| 2013/0281947 A1 | 10/2013 | Quisenberry |
| 2013/0331767 A1 | 12/2013 | Quisenberry |
| 2014/0012169 A1 | 1/2014 | Wilford et al. |
| 2014/0046410 A1 | 2/2014 | Wyatt |
| 2014/0052054 A1 | 2/2014 | Quisenberry |
| 2014/0236271 A1 | 8/2014 | Fronda et al. |
| 2014/0257175 A1 | 9/2014 | Quisenberry |
| 2014/0316330 A1 | 10/2014 | Fudem et al. |
| 2014/0323949 A1 | 10/2014 | Quisenberry |
| 2015/0133849 A1 | 5/2015 | Quisenberry et al. |
| 2015/0290364 A1 | 10/2015 | Wall et al. |
| 2015/0328042 A1 | 11/2015 | Parish et al. |
| 2016/0030236 A1 | 2/2016 | Parish et al. |
| 2016/0067104 A1 | 3/2016 | Sarangapani et al. |
| 2016/0082238 A1 | 3/2016 | Wells et al. |
| 2016/0317348 A1 | 11/2016 | Banker |
| 2017/0119940 A1 | 5/2017 | Quisenberry |

FOREIGN PATENT DOCUMENTS

| | | | |
|---|---|---|---|
| EP | 0076074 A1 | | 4/1983 |
| EP | 0 489 326 | | 6/1992 |
| GB | 2373444 A | | 9/2002 |
| JP | 2009504246 A | | 2/2009 |
| SU | 689674 | | 10/1979 |
| WO | WO-1989009583 A2 | | 10/1989 |
| WO | WO-93/09727 | | 5/1993 |
| WO | WO-93/12708 A2 | | 7/1993 |
| WO | WO-1996005873 A1 | | 2/1996 |
| WO | WO-9807397 A1 | | 2/1998 |
| WO | WO-1998016176 A1 | | 4/1998 |
| WO | WO-00/40186 | | 7/2000 |
| WO | WO-01/14012 A1 | | 3/2001 |
| WO | WO-01/54635 A1 | | 8/2001 |
| WO | WO-2004105676 A1 | | 12/2004 |
| WO | WO-2005046760 A1 | | 5/2005 |
| WO | WO-2007019038 A2 | | 2/2007 |
| WO | WO-2008099017 A1 | | 8/2008 |
| WO | WO-2010124234 A1 | | 10/2010 |
| WO | WO-2012067918 A1 | | 5/2012 |

OTHER PUBLICATIONS

U.S. Appl. No. 14/062,428, Quisenberry.
U.S. Appl. No. 14/197,324, Quisenberry.
U.S. Appl. No. 12/730,060, Parish et al.
U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
U.S. Appl. No. 13/190,564, Quisenberry et al.
U.S. Appl. No. 29/397,856, Quisenberry.
U.S. Appl. No. 29/400,194, Quisenberry.
U.S. Appl. No. 19/400,202, Quisenberry.
U.S. Appl. No. 29/400,212, Quisenberry.
U.S. Appl. No. 29/401,115, Quisenberry.
Artikis, T., PCT International Preliminary Report on Patentability dated Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 dated Apr. 2, 2008, 2 pages.
Young, Lee W., "International Search Report" for PCT/US07/08807 dated Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al.,"Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Quisenberry, Tony, "U.S. Appl. No. 13/359,210", filed Jan. 26, 2012.
Quisenberry, Tony, "U.S. Appl. No. 29/424,860", filed Jun. 15, 2012.
Quisenberry, Tony, "U.S. Appl. No. 13/456,410", filed Apr. 26, 2012.
Copenheaver, Blaine R., "International Search Report" for PCT/US2012/035096 dated Aug. 7, 2012, 3 pages.
Quisenberry, Tony, "U.S. Appl. No. 13/558,615", filed Jul. 26, 2012.
Copenheaver, Blaine R., "International Search Report" prepared for PCT/US2013/030475 dated May 23, 2013, 3 pages.
U.S. Appl. No. 13/962,994, Quisenberry.
Young, Lee W., International Search Report of PCT Application No. PCT/US2014/64805, dated Mar. 13, 2015 (3 pages).
U.S. Appl. No. 15/227,417, Aug. 3, 2016, Overton et al.
U.S. Appl. No. 15/370,689, Quisenberry.
Hair Science Systems LLC, "Hair Science Systems—01 mobile unit—", Hair Saver Chemo Cold Cap, www.hairsciencesystems.com, 2 pages.
"U.S. FDA de novo clearance for the DigniCap® scalp cooling system that reduces hair loss related to chemotherapy for women with breast cancer", www.sysmex-europe.com/company/news-and-events/press-releases, accessed on Jun. 17, 2016, 3 pages.
"DigniLife—Prevention of Chemotherapy-Induced Alopecia", www.sysmex.co.uk/products/oncology/scalp-cooling-system-dignilife, accessed on Jun. 17, 2016, 3 pages.

* cited by examiner

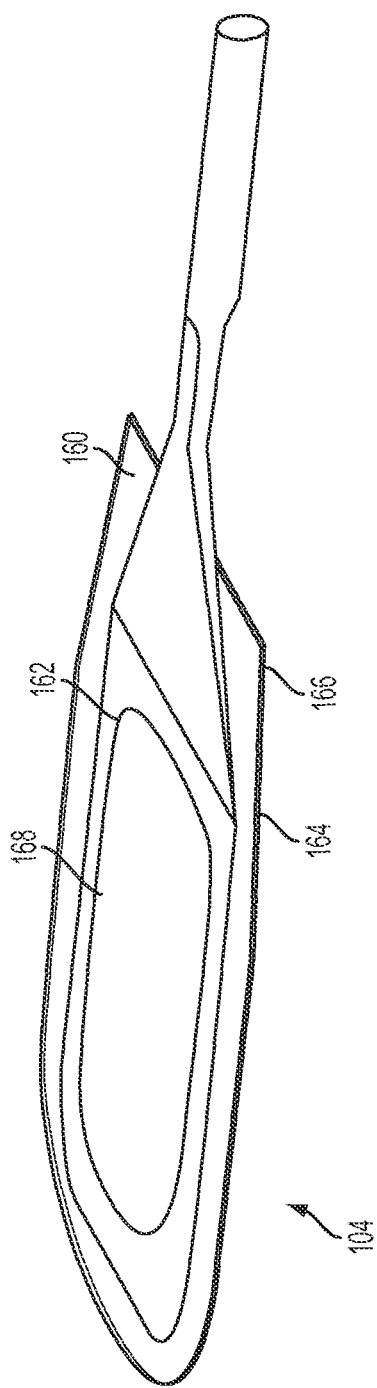

METHOD AND SYSTEM FOR THERAPEUTIC USE OF ULTRA-VIOLET LIGHT

CROSS-REFERENCE TO RELATED APPLICATIONS

This application claims the benefit of U.S. Provisional Patent Application No. 61/637,601, filed Apr. 24, 2012. In addition, U.S. patent application Ser. No. 13/107,264, filed May 13, 2011, U.S. patent application Ser. No. 11/801,662 (now U.S. Pat. No. 8,100,956), filed May 9, 2007, U.S. patent application Ser. No. 13/190,564 (now U.S. Pat. No. 8,142,486), filed Jul. 26, 2011, U.S. patent application Ser. No. 13/359,210, filed Jan. 26, 2012, U.S. patent application Ser. No. 13/456,410, filed Apr. 26, 2012, U.S. patent application Ser. No. 11/975,047 (now U.S. Pat. No. 8,128,672), filed Oct. 17, 2007, and U.S. Provisional Patent Application No. 61/637,601 are each incorporated herein by reference.

BACKGROUND

Field of the Invention

The present application relates generally to a wound care method and system utilizing pulsed ultra-violet light therapy and more particularly, but not by way of limitation, to a wound care method and system utilizing a thermoelectric element for thermal management of an array of ultra-violet light-emitting diodes.

History of the Related Art

An important aspect of patient treatment is wound care. Medical facilities are constantly in need of advanced technology for cleaning and treatment of skin wounds. Larger skin wounds present more serious issues of wound closure and infection prevention. The rapidity of migration over the wound of epithelial and subcutaneous tissue adjacent the wound is thus critical. Devices have been developed and/or technically described which address certain aspects of such wound healing. For example, U.S. Pat. No. 6,695,823 to Lina et al. ("Lina") describes a wound therapy device that facilitates wound closure. A vacuum pump is taught for collecting fluids from the wound. WO 93/09727 discloses a solution for wound drainage by utilizing negative pressure over the wound to promote migration of epithelial and subcutaneous tissue over the wound.

Wound treatment may also be performed using light therapy. For example, U.S. Pat. No. 7,081,128 to Hart et al. ("Hart") describes a method of treating various medical conditions such as, for example, joint inflammation, edema, etc., utilizing an array of Light Emitting Diodes ("LEDs") contained on a flexible substrate that may be wrapped around an anatomical feature of a human body. U.S. Pat. No. 6,596,016 to Vreman et al. ("Vreman") discloses a phototherapy garment for an infant having a flexible backing material, a transparent liner, and a flexible printed circuit sheet containing surface-mounted LEDs. The LEDs preferably emit high-intensity blue light, suitable for treatment of neonatal hyperbilirubinemia. The device may include a portable power supply.

SUMMARY

The present application relates generally to a wound care method and system utilizing pulsed ultra-violet light therapy and more particularly, but not by way of limitation, to a wound care method and system utilizing a thermoelectric element for thermal management of an array of ultra-violet light-emitting diodes. In one aspect, the present invention relates to a wound care system. The wound care system includes a power unit and a processor coupled to the power unit. An ultra-violet light-emitting diode array is electrically coupled to the processor. A thermoelectric element is thermally exposed to the ultra-violet light-emitting diode array. A probe is optically coupled to the ultra-violet light-emitting diode array. The thermoelectric element cools the ultra-violet light emitting diode array thereby optimizing the ultra-violet light emitting diode array.

In another aspect, the present invention relates to a method for treating a wound area. The method includes coupling a probe to a control unit via a control fiber port and applying the probe to a wound area. The method further includes generating ultra-violet light via an ultra-violet light-emitting diode array and providing the ultra-violet light to the wound area via the probe. The method further includes cooling the ultra-violet light-emitting diode array via a thermoelectric element.

BRIEF DESCRIPTION OF THE DRAWINGS

For a more complete understanding of the present invention and for further objects and advantages thereof, reference may now be had to the following description taken in conjunction with the accompanying drawings in which:

FIG. 1D is a perspective view of a patch probe according to an exemplary embodiment;

DETAILED DESCRIPTION

Various embodiments of the present invention will now be described more fully with reference to the accompanying drawings. The invention may, however, be embodied in many different forms and should not be construed as limited to the embodiments set forth herein.

Figure 1A:
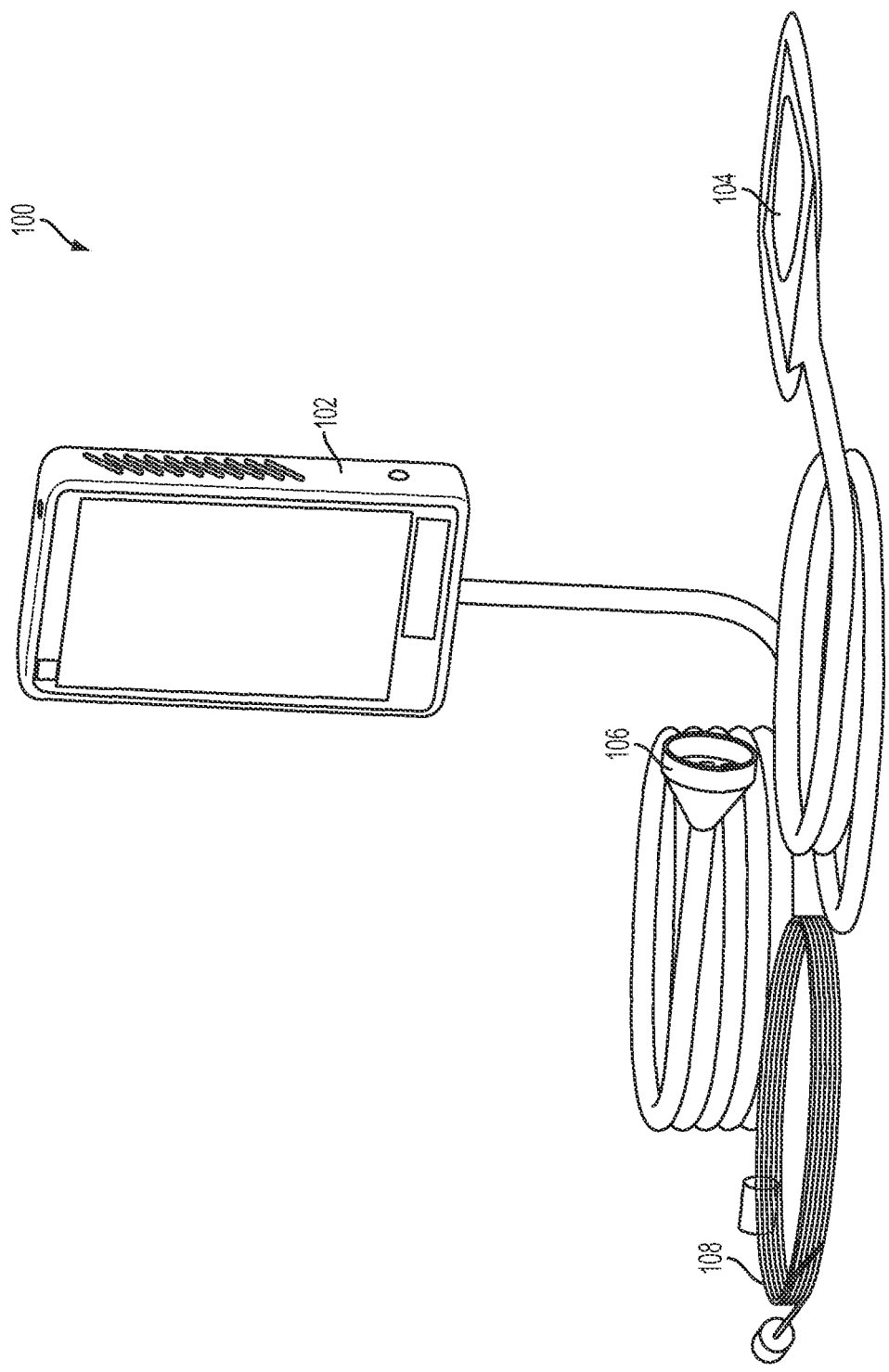
FIG. 1A is a perspective view of a therapeutic system according to an exemplary embodiment.

FIG. 1A is a perspective view of a therapeutic system 100 according to an exemplary embodiment. The therapeutic system 100 includes a control unit 102 optically coupled to at least one of a patch probe 104, a spot probe 106, and a point probe 108. In various embodiments, a belt clip (not shown) is disposed on a rear surface of the control unit 102. As will be discussed in more detail herein below, the patch probe 104, the spot probe 106, and the point probe 108 are interchangeable with each other and are adapted to be optically coupled to the control unit 102.

Figure 1B:
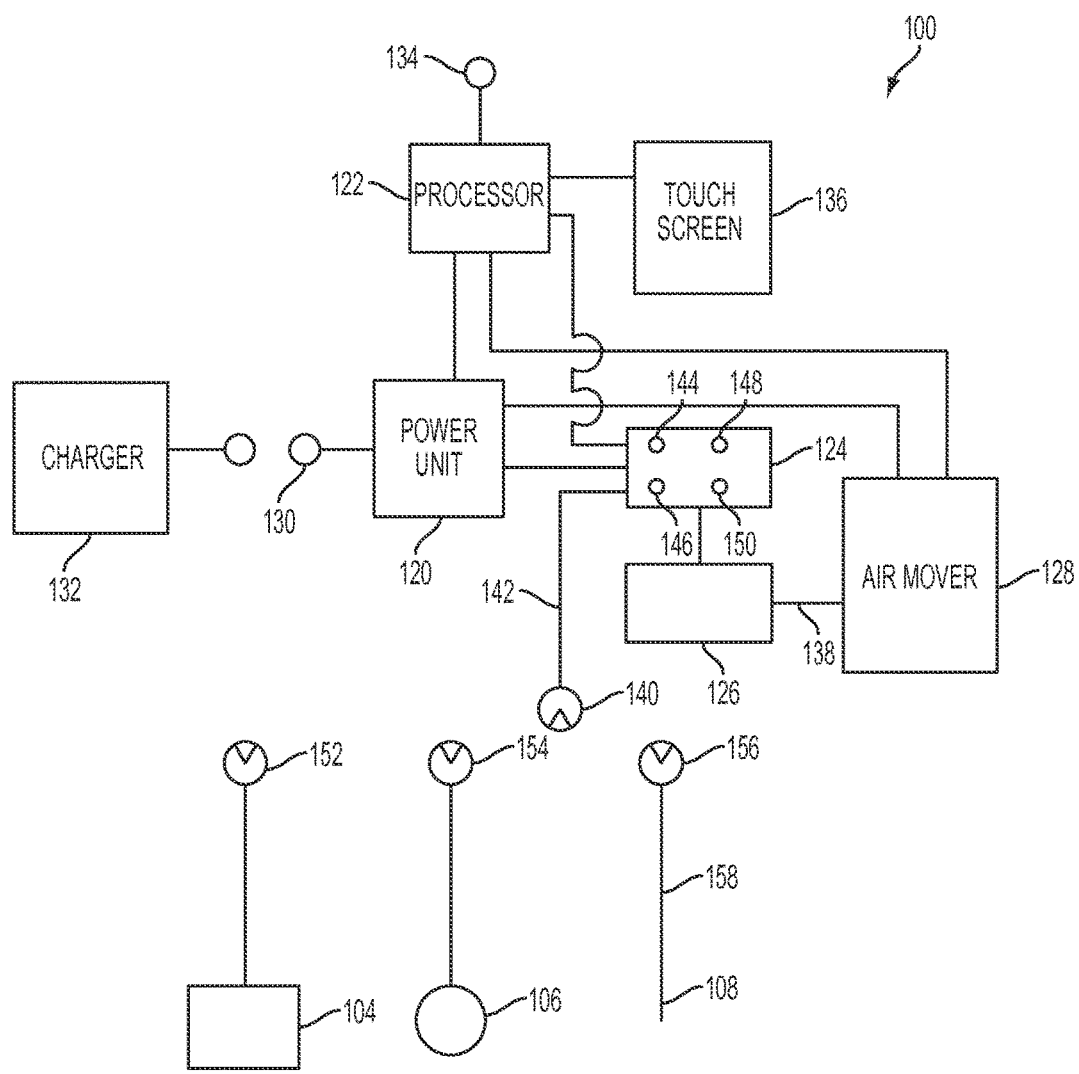
FIG. 1B is a schematic diagram of the therapeutic system of FIG. 1 according to an exemplary embodiment.

FIG. 1B is a schematic diagram of the therapeutic system 100 according to an exemplary embodiment. The control unit 102 (shown in FIG. 1) includes a power unit 120 electrically coupled to a processor 122, an ultra-violet light-emitting diode ("LED") array 124, a thermoelectric element 126, and an air mover 128. In a typical embodiment, the power unit 120 is, for example, a battery, a fuel cell, or other appropriate power source as dictated by design requirements. Fuel cells are utilized in remote locations such as, for example, rural locations, research stations, and military applications. Fuel cells are typically compact, lightweight, and have no major moving parts. The power unit 120 is electrically coupled to a charge port 130. The charge port 130 is arranged to be electrically coupled to a charger 132. In a typical embodiment, the charger 132 is operable to be removeably coupled to the charge port 130 and supply an electrical charge to the power unit 120. In a typical embodiment, the charger 132 may utilize, for example, alternating-current ("AC") power or direct-current ("DC") power.

The processor 122 is electrically coupled to the power unit 120, the LED array 124, and the air mover 128. The processor 122 includes a power switch 134 and a touch screen 136. In a typical embodiment, the touch screen 136 allows adjustment of a plurality of treatment parameters such as, for example, a treatment time, a LED intensity, and the like. In a typical embodiment, the processor 122 may be, for example, a microprocessor.

The air mover 128 is electrically coupled to the processor 122 and the power unit 120. In a typical embodiment, the air mover 128 may be, for example, a turbine, a fan, or other device as dictated by design requirements. The air mover 128 is fluidly coupled to a warm side of the thermoelectric element 126 via an exhaust port 138. In a typical embodiment, the air mover 128 facilitates removal of heat from a warm side of the thermoelectric element 126.

The LED array 124 is electrically coupled to the power unit 120 and the processor 122. The LED array 124 is optically coupled to a control fiber port 140 via a plurality of fiber-optic strands 142. The LED array 124 includes a first diode 144, a second diode 146, a third diode 148, and a fourth diode 150. The first diode 144, the second diode 146, and the third diode 148 generate light having a wavelength in the range of approximately 400 nm to approximately 315 nm, commonly referred to as UV-A light. The fourth diode 150 generates light having a wavelength in the range of approximately 100 nm to approximately 280 nm, commonly referred to as UV-C light. Although the LED array 124 is shown and described herein as including the first diode 144, the second diode 146, the third diode 148, and the fourth diode 150, LED arrays utilizing principles of the invention may, in other embodiments, include any number of diodes. The control fiber port 140 is adapted for connection of at least one of the patch probe 104, the spot probe 106, and the point probe 108. The LED array 124 is thermally exposed to a cold side of the thermoelectric element 126.

The processor 122 modulates ultraviolet light generated by the LED array 124 to create various patterns of light, various intensities of light, and various durations of light. In a typical embodiment, the first diode 144, the second diode 146, and the third diode 148 generate approximately continuous UV-A light for application to, for example, a wound area. In other embodiments, the first diode 144, the second diode 146, and the third diode 148 generate pulsed emissions of UV-A light. In a typical embodiment, the fourth diode 150 generates pulsed emissions of UV-C light for application to the wound area. In a typical embodiment, the fourth diode 150 generates UV-C light for a duration of, for example, approximately three minutes approximately every twelve hours.

The patch probe 104 is optically coupled to a patch fiber port 152. The spot probe 106 is optically coupled to a spot fiber port 154. The point probe 108 is optically coupled to a point fiber port 156. The patch fiber port 152, the spot fiber port 154, and the point fiber port 156 are adapted to be removeably coupled to the control fiber port 140 thereby facilitating transmission of ultra-violet light from the LED array 124 to at least one of the patch probe 104, the spot probe 106, and the point probe 108.

During operation, the LED array 124 transmits ultra-violet light to at least one of the patch probe 104, the spot probe 106, and the point probe 108 via the plurality of fiber-optic strands 142 and the control fiber port 140. In a typical embodiment, the first diode 144, the second diode 146, and the third diode 148 generate approximately continuous UV-A light for application to, for example, a wound area. In other embodiments, the first diode 144, the second diode 146, and the third diode 148 generate pulsed emissions of UV-A light. In a typical embodiment, the fourth diode 150 generates pulsed emissions of UV-C light for application to the wound area. In a typical embodiment, the fourth diode 150 generates UV-C light for a duration of, for example, approximately three minutes approximately every twelve hours. The thermoelectric element 126 facilitates removal of excess heat generated by the LED array 124 thus cooling the LED array 124. It has been shown that approximately 70% of energy generated by an LED array such as, for example, the LED array 124, is heat energy rather than light. If excess heat is not removed from the LED array 124, an efficiency and reliability of the LED array 124 is negatively impacted. Thus, cooling the LED array 124, via the thermoelectric element 126, optimizes the LED array 124 and improves therapeutic efficacy of the therapeutic system 100. The thermoelectric element 126 transfers the excess heat to the exhaust port 138. The air mover 128 circulates air in the exhaust port 138 with an environment.

Ultra-violet light provided by the LED array 124 promotes wound healing and human tissue growth. Energy delivered by the LED array 124 enhances cellular metabolism, accelerates repair and replenishment of damaged skin cells, and stimulates production of collagen which is a foundation of healthy and smooth skin. Ultra-violet light therapy is non-ablative, non-invasive, and painless. Ultra-violet light is capable of penetrating through several layers of skin to destroy infectious bacteria. According to exemplary embodiments, the ultraviolet light from the LED array 124 is in the range of approximately 100 to approximately 450 nanometers and higher, and energy levels of up to approximately 35,000 microwatt seconds/cm$^2$, which are necessary to eliminate or destroy microorganisms such as, for example, bacteria, spores, algae and viruses. Most bacteria can be destroyed at ultra-violet energies of about 3,000 to about 5,000 microwatt-seconds/cm$^2$ while mold spores may require energies of about 20,000 to about 35,000 mW-seconds/cm$^2$.

The point probe 108 includes at least one fiber-optic strand 164 optically coupled to the point fiber port 156. In some embodiments, point probes utilizing principles of the invention may include a single fiber-optic strand. In some embodiments, the point probe 108 may be adapted as a catheter suitable for intravenous use. In still other embodiments, the point probe 108 may be adapted for point treatment of a surface wound.

Figure 1C:
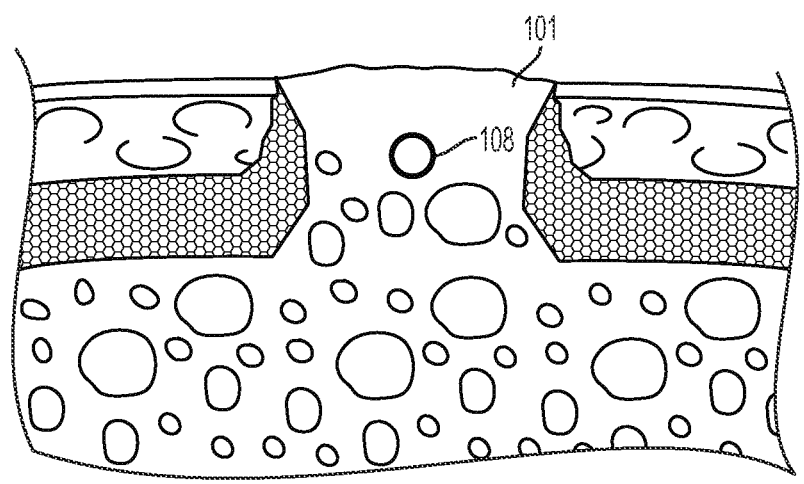
FIG. 1C is a schematic diagram that illustrates use of a point probe of the therapeutic system of FIG. 1A according to an exemplary embodiment.

FIG. 1C is a schematic diagram illustrating use of the point probe 108 during treatment of a wound area according to an exemplary embodiment. The point probe 108 is placed in a wound area 101. In a typical embodiment, ultra-violet light is thus applied to an interior of the wound area 101 via the at least one fiber-optic strand 158. Ultra-violet light, delivered to the wound area 101 via the point probe 108, promotes healing of the wound area 101 and human tissue growth. Energy delivered via the point probe 108 enhances cellular metabolism, accelerates repair and replenishment of damaged skin cells, and stimulates production of collagen which is a foundation of healthy and smooth skin.

FIG. 1D is a perspective view of the patch probe 104 according to an exemplary embodiment. The patch probe 104 includes a first layer 160 having a first gap 162 formed therein and a second layer 164 having a second gap (not shown) formed therein. The first layer 160 and the second layer 164 are constructed of, for example, urethane and are coupled to each other along a perimeter via a process such as, for example, welding. The second layer 164 includes an adhesive bottom surface 166. A fiber-optic array 168 is disposed between the first layer 160 and the second layer 164 so as to fill a space defined by the first gap 162 and the second gap. The fiber-optic array 168 is optically coupled to the patch fiber port 152 (shown in FIG. 1B).

Figure 1E:
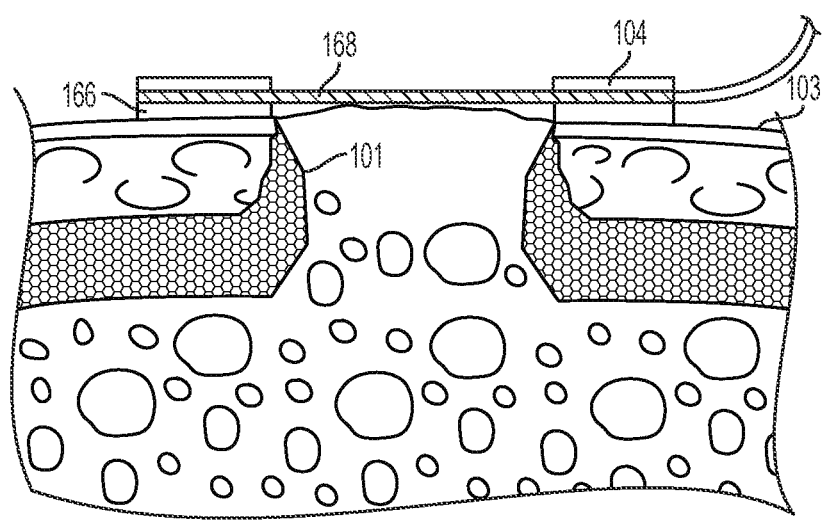
FIG. 1E is a schematic diagram that illustrates use of the patch probe of FIG. 1D according to an exemplary embodiment.

FIG. 1E is a schematic diagram illustrating use of the patch probe 104 according to an exemplary embodiment. During operation, the adhesive bottom surface 166 is applied to a skin area 103 surrounding the wound area 101. The fiber optic array 168 is placed in direct contact with the wound area 101. Ultra-violet light is thus applied to the wound area 101 via the fiber-optic array 168. Ultra-violet light delivered to the wound area 101 via the patch probe 104 promotes healing of the wound area 101 and human tissue growth. Energy delivered via the patch probe 104 enhances cellular metabolism, accelerates repair and replenishment of damaged skin cells, and stimulates production of collagen which is a foundation of healthy and smooth skin.

Figure 1F:
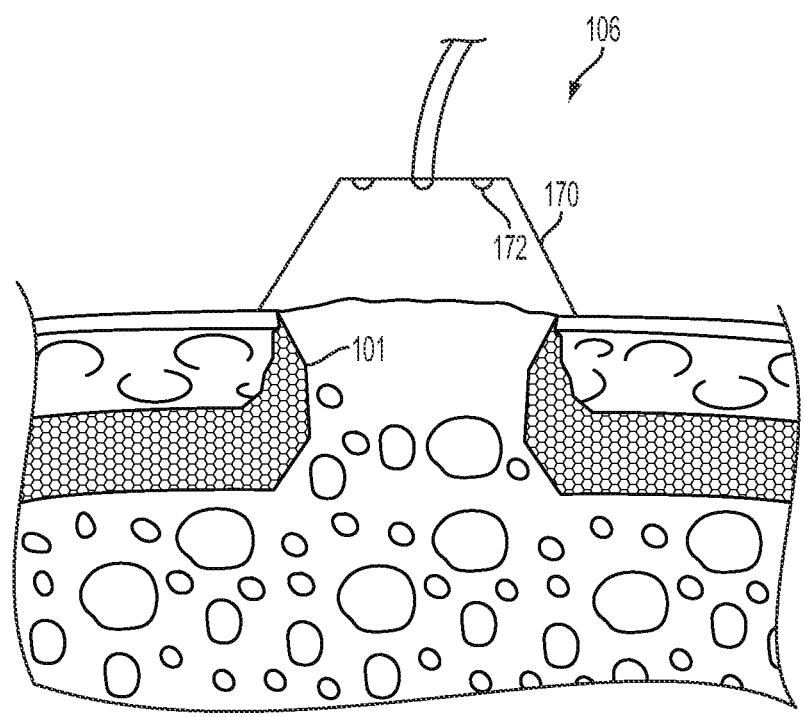
FIG. 1F is a cross-sectional plan view of a spot probe according to an exemplary embodiment.

FIG. 1F is a schematic diagram illustrating use of the spot probe 106 according to an exemplary embodiment. The spot probe 106 includes a shell 170 having a plurality of fiber-optic strand ends 172 disposed therein. The plurality of fiber-optic strand ends 172 are optically coupled to the spot fiber port 154 (shown in FIG. 1B). During operation, the shell 170 is placed over the wound area 101 thereby allowing treatment of the wound area 101 via the plurality of fiber-optic strand ends 172. Ultra-violet light delivered to the wound area 101 via the spot probe 106 promotes healing of the wound area 101 and human tissue growth. Energy delivered via the spot probe 106 enhances cellular metabolism, accelerates repair and replenishment of damaged skin cells, and stimulates production of collagen which is a foundation of healthy and smooth skin.

Figure 1G:
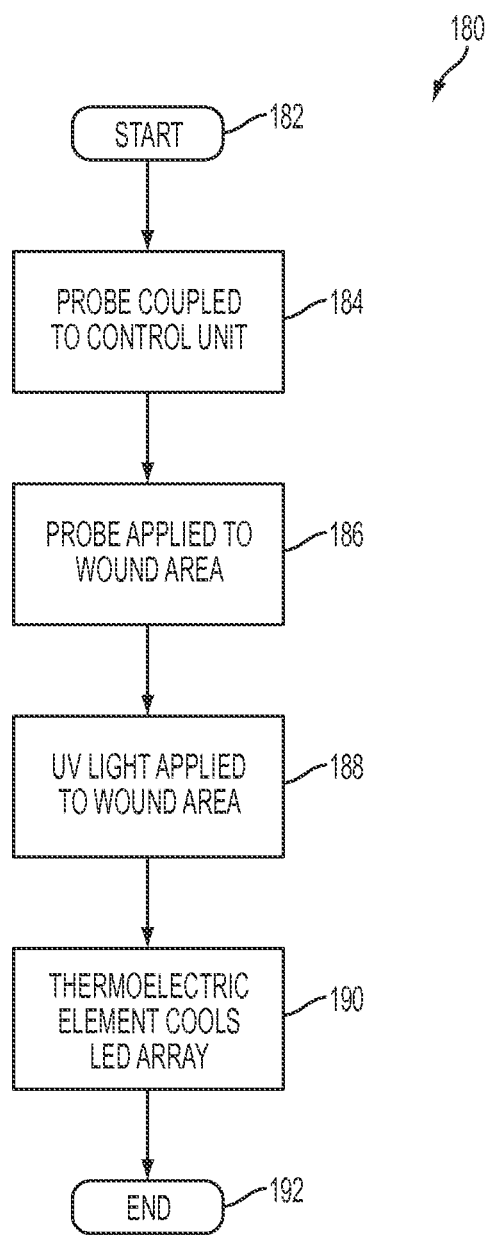
FIG. 1G is a flow diagram of a process for treating a wound area according to an exemplary embodiment.

FIG. 1G is a flow diagram of a process for treating a wound area according to an exemplary embodiment. The process 180 begins at step 182. At step 184, at least one of the patch probe 104, the point probe 108, and the spot probe 106 are coupled to the control unit 102 via the control fiber port 140. At step 186, at least one of the patch probe 104, the spot probe 106, and the point probe 108 is applied to a wound area of a patient. At step 188, ultra-violet light is applied to the wound area via at least one of the patch probe 104, the spot probe 106, and the point probe 108. At step 190, the thermoelectric element 126 cools the LED array 124 thereby optimizing the LED array 124. The process 180 ends at step 192.

Figure 2A:
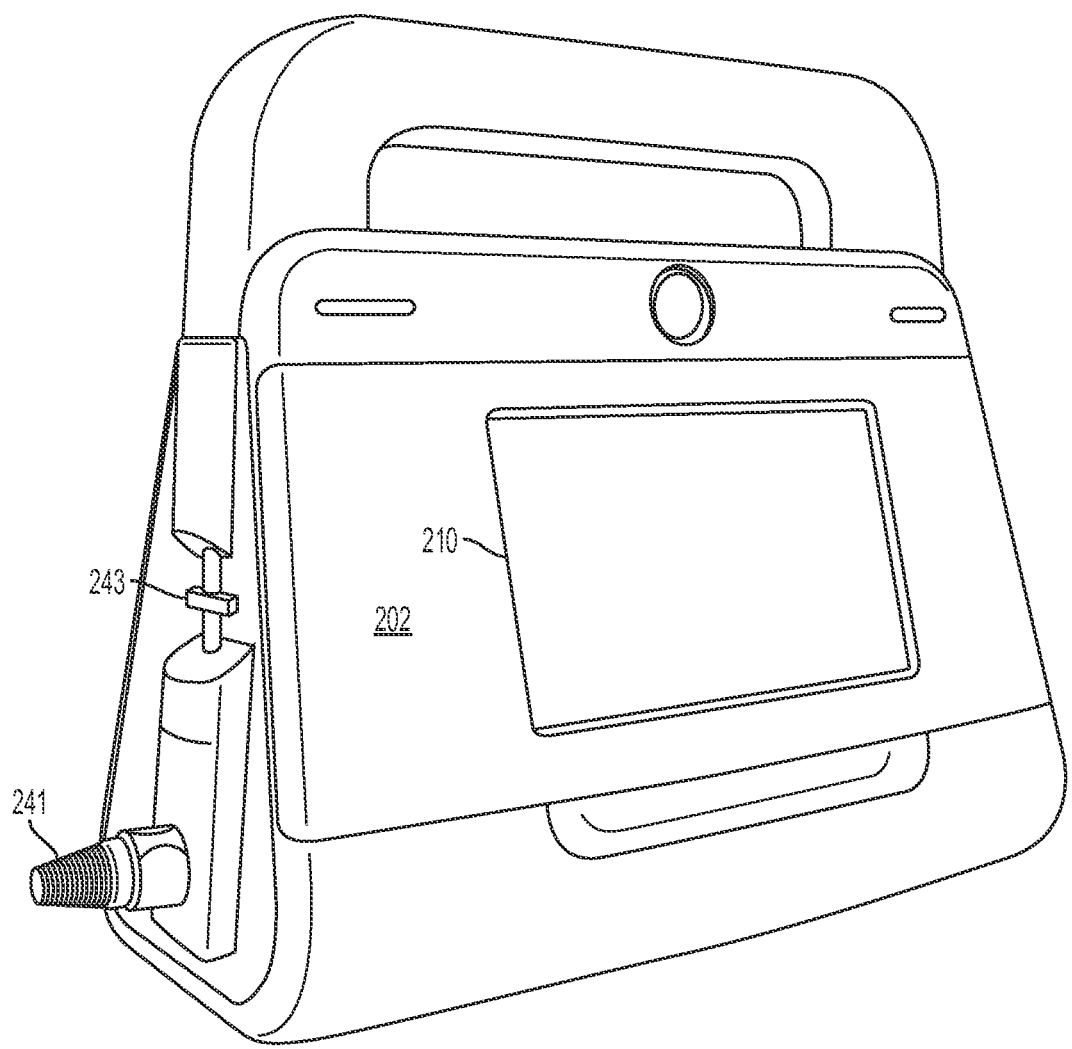
FIG. 2A is a perspective view of a therapeutic system including vacuum therapy according to an exemplary embodiment.

FIG. 2A is a perspective view of a therapeutic system 200 including vacuum therapy according to an exemplary embodiment. The therapeutic system 200 includes a control unit 202. The control unit 202 includes a control fiber port 241 and a fluid port 243. In a typical embodiment, the control fiber port 241 is optically coupled to a probe 245 via optical fibers. In a typical embodiment, the probe 245 is fluidly coupled to the fluid port 243 via a fluid line. A touch screen interface 210 is disposed on a front of the control unit 202. In a typical embodiment, the touch screen interface 210 utilizes an operating system such as, for example, Android 4.0 operating system, available from Google, Inc., or other similar operating system. In various embodiments, the probe 241 may be at least one of, for example, a patch probe 253 (shown in FIG. 2D), a point probe 248 (shown in FIG. 2C), and a spot probe 262 (shown in FIG. 2E).

Figure 2B:
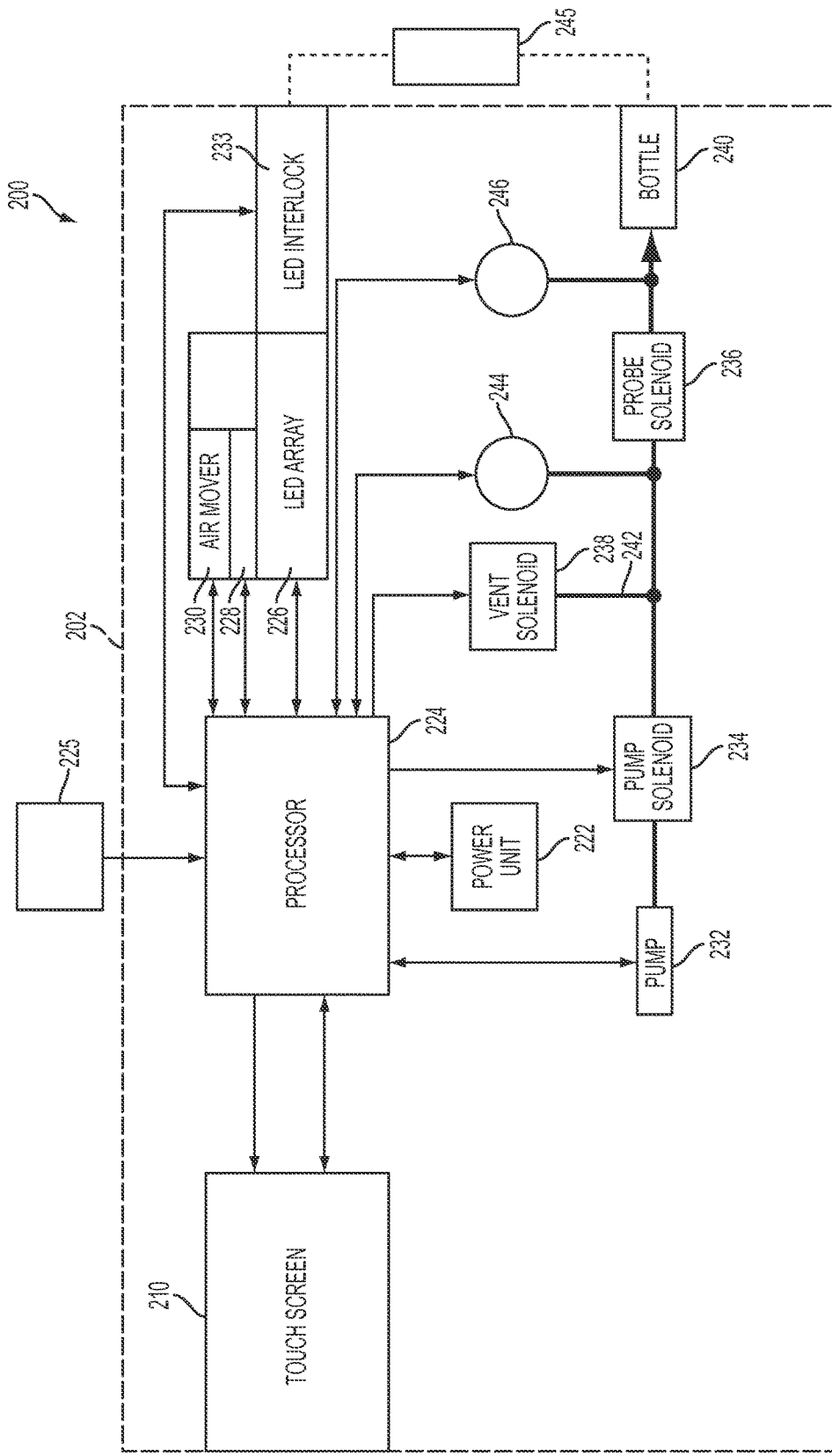
FIG. 2B is a schematic diagram of the therapeutic system of FIG. 2A according to an exemplary embodiment.

FIG. 2B is a schematic diagram of the therapeutic system 200 according to an exemplary embodiment. The control unit 202 (shown in FIG. 2A) includes a power unit 222 electrically coupled to a processor 224, an ultra-violet light-emitting diode ("LED") array 226, a thermoelectric element 228, and an air mover 230. In a typical embodiment, the power unit 222, the processor 224, the LED array 226, the thermoelectric element 228, and the air mover 230 are similar in construction and operation to the power unit 120, the processor 122, the LED array 124, the thermoelectric element 126, and the air mover 128 discussed above with respect to FIG. 1B. A charge module 225 is electrically coupled to the processor 224. In a typical embodiment, the charge module 225 may be, for example, an alternating current ("AC") adapter. In a typical embodiment, the charge module facilitates charging of the power unit 222.

Still referring to FIG. 2B, the therapeutic system includes a pump 232 electrically coupled to the processor 224, a pump solenoid 234, a probe solenoid 236, a vent solenoid 238, and an exudate bottle 240. The pump solenoid 234, the probe solenoid 236, the vent solenoid 238, and the exudate bottle 240 are fluidly coupled to the pump 232. In addition, the pump solenoid 234, the probe solenoid 236, the vent solenoid 238 are electrically coupled to the processor 224. In a typical embodiment, the pump 232 operates in at least one of a high vacuum state and a low vacuum state. In the high vacuum state, the pump generates vacuum pressure in the range of approximately 75 mmHg to approximately 150 mmHg while, in the low vacuum state, the pump generates vacuum pressure in the range of approximately 25 mmHg to approximately 75 mmHg.

Still referring to FIG. 2B, an LED interlock 233 is electrically coupled to the processor 224 and optically coupled to the LED array 226. During operation, the LED interlock 233 prompts the processor 224 to deactivate the LED array 226 upon disconnection of a probe from the control fiber port 241. Such an arrangement prevents injury to, for example, an eye of a user.

Still referring to FIG. 2B, the pump solenoid 234 is fluidly coupled to the pump 232 and disposed between the pump 232 and a vent 242. The pump solenoid 234, when open, fluidly couples the pump 232 to the vent 242 and the probe solenoid 236. When closed, the pump solenoid 234 isolates the pump 232 from the vent 242. The vent solenoid 238 is fluidly coupled to the vent 242 between the pump solenoid 234 and the probe solenoid 236. When open, the vent solenoid 238 allows gas to escape to an atmosphere via the vent 242 and relieves vacuum pressure applied to the probe 245. When closed, the vent solenoid 238 prevents relief of vacuum pressure. The probe solenoid 236 is fluidly coupled to the pump solenoid 234 and the exudate bottle 240. The probe solenoid 236 is disposed between a first pressure sensor 244 and a second pressure sensor 246. When open, the probe solenoid 236 fluidly couples pump solenoid 234 to the exudate bottle 240. When closed, the probe solenoid 236 isolates, the exudate bottle 240 and the probe 245. Isolation of the exudate bottle 240 and the probe 245 allows the probe 245 to be tested, via the first pressure sensor 244 and the second pressure sensor 246, to ensure that a sufficient seal is present between the probe 245 and the wound site.

Still referring to FIG. 2B, during operation, the pump 232 operates in at least one of the high vacuum state or the low vacuum state. The processor directs the vent solenoid 238 to close thus preventing release of gas to the atmosphere. The processor directs the pump solenoid 234 and the probe solenoid 236 to open thus fluidly connecting the pump 232 to the exudate bottle 240 and the probe 245. Such an arrangement provides vacuum therapy to a wound site and removes fluid, contaminants, dead tissue, and other undesirable materials from the wound site. The fluid, contaminants, dead tissue, and other undesirable materials are collected in the exudate bottle 240.

Still referring to FIG. 2B, during operation, if a desired level of vacuum is exceeded, the processor 224 directs the vent solenoid 238 to open thereby relieving the vacuum applied to the wound area. Thus, the processor 224 maintains a desired level of vacuum via selective opening and closing of the pump solenoid 234 and the vent solenoid 238.

Figure 2C:
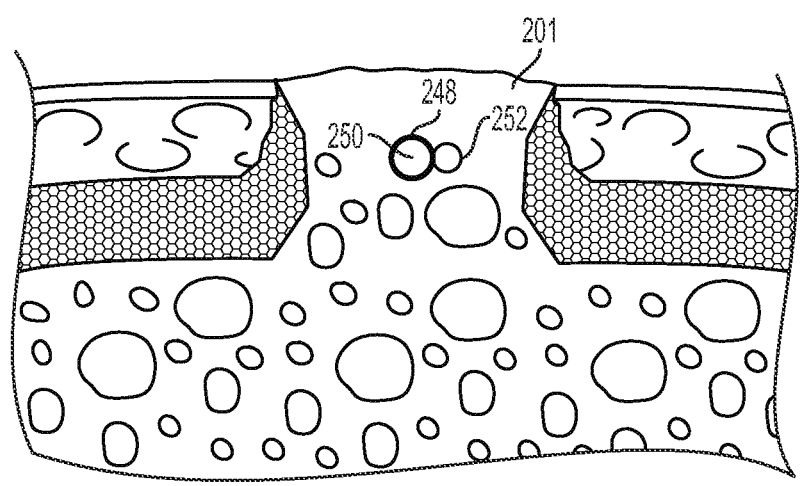
FIG. 2C is a schematic diagram illustrating use of a point probe during treatment of a wound area according to an exemplary embodiment.

FIG. 2C is a schematic diagram illustrating use of a point probe 248 during treatment of a wound area according to an exemplary embodiment. The point probe 248 is placed in a wound area 201. Ultra-violet light is thus applied to an interior of the wound area 201 via the at least one fiber-optic strand 250. Vacuum pressure is applied to the wound area 201 via at least one tube 252, which is joined to the at least one fiber-optic strand 250. The at least one tube 252 is in fluid communication with the pump 232 and the exudate bottle 240 (shown in FIG. 2B). Vacuum pressure delivered to the wound area 201 via the point probe 248 removes accumulated fluid, dead tissue, and other undesirable materials from the wound area 201. Ultra-violet light delivered to the wound area 201 via the point probe 248 promotes healing of the wound area 201 and human tissue growth. Energy delivered via the point probe 248 enhances cellular metabolism, accelerates repair and replenishment of damaged skin cells, and stimulates production of collagen which is a foundation of healthy and smooth skin.

Figure 2D:
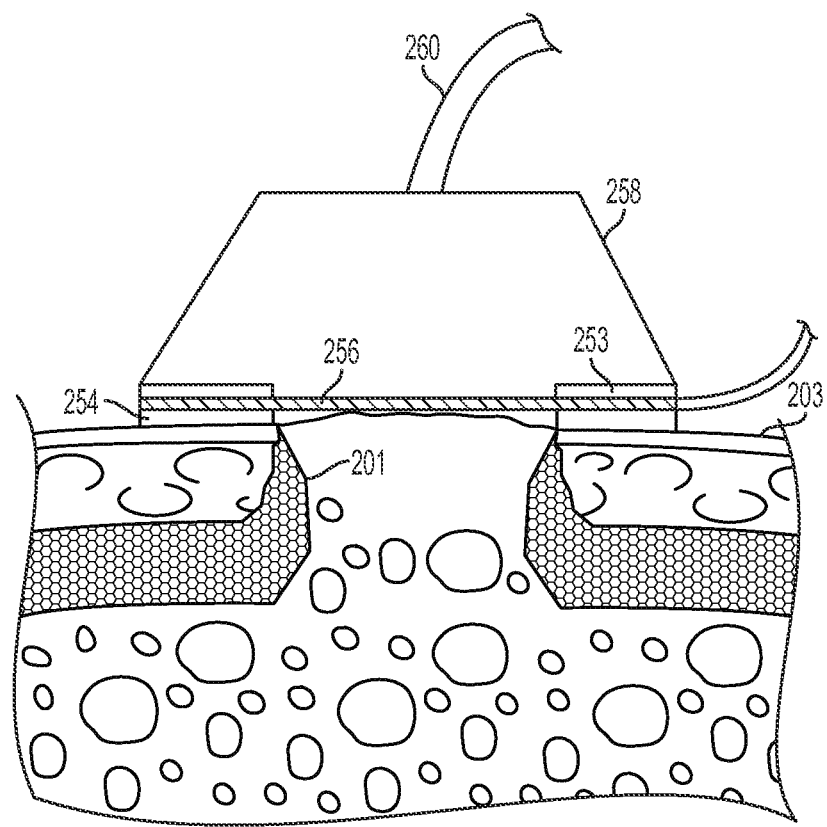
FIG. 2D is a schematic diagram illustrating use of a patch probe according to an exemplary embodiment.

FIG. 2D is a schematic diagram illustrating use of the patch probe 253 according to an exemplary embodiment. During operation, an adhesive bottom surface 254 is applied to a skin area 203 surrounding the wound area 201. A fiber optic array 256 is placed in direct contact with the wound area 201. A recess 258 is formed above the fiber optic array 256. A tube 260 is fluidly coupled to the recess 258. The tube 260 is in fluid communication with the pump 232 and the exudate bottle 240 (shown in FIG. 2B). During operation, vacuum pressure is applied to the wound area 201 via the tube 260. Vacuum pressure delivered to the wound area 201 via the patch probe 253 removes accumulated fluid, dead tissue, and other undesirable materials from the wound area 201. In a typical embodiment, the fiber-optic array 256 is porous so as to allow removal of the accumulated fluid, dead tissue, and other undesirable materials from the wound area 201. Ultra-violet light is applied to the wound area 201 via the fiber-optic array 256. Ultra-violet light delivered to the wound area 201 via the patch probe 253 promotes healing of the wound area 201 and human tissue growth. Energy delivered via the patch probe 253 enhances cellular metabolism, accelerates repair and replenishment of damaged skin cells, and stimulates production of collagen which is a foundation of healthy and smooth skin.

Figure 2E:
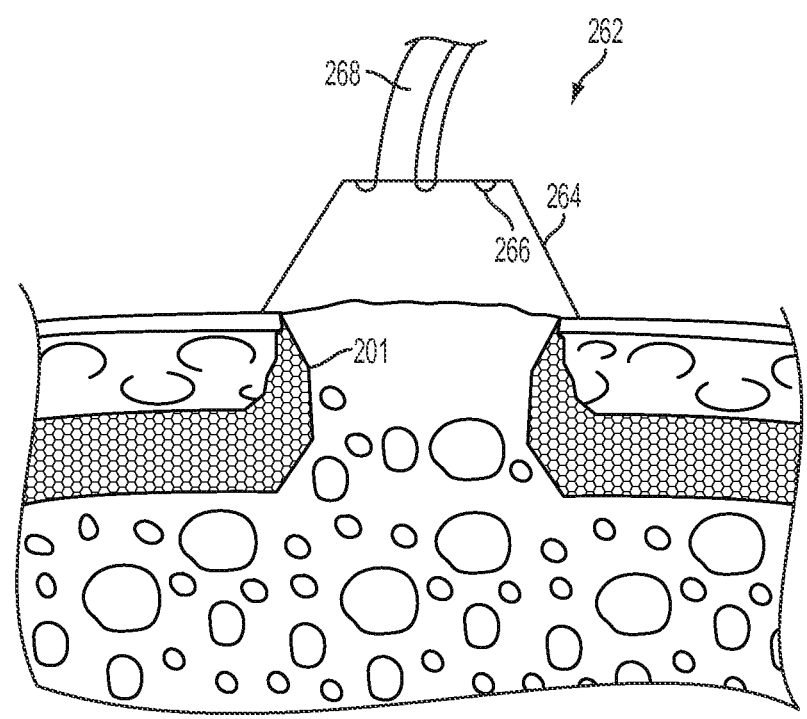
FIG. 2E is a schematic diagram illustrating use of a spot probe according to an exemplary embodiment.

FIG. 2E is a schematic diagram illustrating use of a spot probe 262 according to an exemplary embodiment. The spot probe 262 includes a shell 264 having a plurality of fiber-optic strand ends 266 disposed therein. The plurality of fiber-optic strand ends 266 are optically coupled to a spot fiber port 154 (not shown). A tube 268 is fluidly coupled to the shell. The tube 268 is in fluid communication with the pump 232 and the exudate bottle 240 (shown in FIG. 2B). During operation, vacuum pressure is applied to the wound area 201 via the tube 268. Vacuum pressure delivered to the wound area 201 via the spot probe 262 removes accumulated fluid, dead tissue, and other undesirable materials from the wound area 201. During operation, the shell 264 is placed over the wound area 201 thereby allowing treatment of the wound area 201 via the plurality of fiber-optic strand ends 266. Ultra-violet light delivered to the wound area 201 via the spot probe 262 promotes healing of the wound area 201 and human tissue growth. Energy delivered via the spot probe 262 enhances cellular metabolism, accelerates repair and replenishment of damaged skin cells, and stimulates production of collagen which is a foundation of healthy and smooth skin.

Figure 2F:
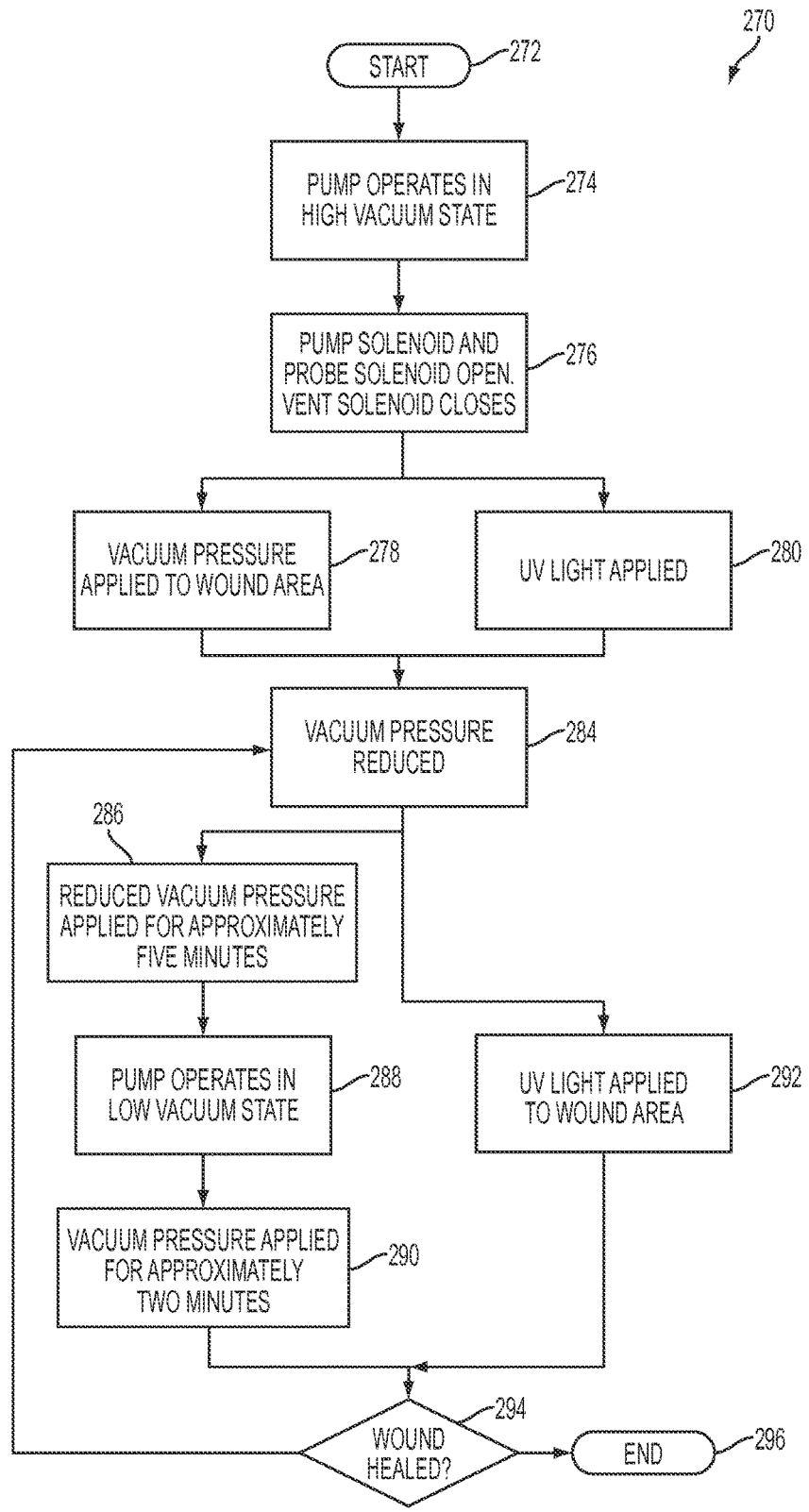
FIG. 2F is a flow diagram of a process for treating a wound according to an exemplary embodiment.

FIG. 2F is a flow diagram of a process for treating a wound according to an exemplary embodiment. A process 270 starts at step 272. At step 274, the processor 224 directs the pump 232 to operate in the high vacuum state. At step 276, the processor 224 directs the pump solenoid 234 and the probe solenoid 236 to open and also directs the vent solenoid 238 to close. At step 278, the pump 232 applies vacuum pressure of, for example, approximately 125 mmHg to the wound area. Such vacuum pressure is applied continuously for approximately 12 hours to approximately 48 hours following, for example, surgery. At step 280, the processor 224 directs the LED array 226 to provide ultra-violet light to the wound area. Such ultraviolet light is applied continuously for approximately 12 hours to approximately 48 hours following, for example, surgery. In particular, as discussed above, UV-A light is applied substantially continuously while UV-C light is applied at approximately three-minute intervals approximately every twelve hours.

Still referring to FIG. 2F, at step 284, the processor 224 directs the pump 232, while operating in the high vacuum state, and the vent solenoid 238 to reduce the level of vacuum pressure applied to the wound area to, for example, approximately 85 mmHg. At step 286, vacuum pressure of, for example, approximately 85 mmHg is applied to the wound area for approximately five minutes. At step 288, the processor 224 directs the pump 232 to operate in the low vacuum state and apply vacuum pressure of, for example, approximately 50 mmHg to the wound area. At step 290, vacuum pressure of, for example, approximately 85 mmHg is applied to the wound area for approximately two minutes. At step 292, the processor directs the LED array 226 to ultraviolet light to the wound area during steps 284-290. At step 294, steps 286-290 are repeated in sequence until the wound area heals. The process ends at step 296.

Although various embodiments of the method and system of the present invention have been illustrated in the accompanying Drawings and described in the foregoing Specification, it will be understood that the invention is not limited to the embodiments disclosed, but is capable of numerous rearrangements, modifications, and substitutions without departing from the spirit and scope of the invention as set forth herein. It is intended that the Specification and examples be considered as illustrative only.

What is claimed is:

1. A wound care system comprising:
a power unit;
a processor coupled to the power unit;
an ultra-violet light-emitting diode array electrically coupled to the processor;
a thermoelectric element thermally exposed to the ultra-violet light-emitting diode array;
a probe optically coupled to the ultra-violet light-emitting diode array;
a pump electrically coupled to the processor and that is fluidly coupled to the probe, the pump applying vacuum pressure to a wound area via the probe;
an exudate bottle fluidly coupled to the pump;
a probe solenoid disposed between, and fluidly coupled, to the pump and the exudate bottle;
a first pressure sensor disposed between the probe solenoid and the pump;
a second pressure sensor disposed between the probe solenoid and the exudate bottle;
wherein, when closed, the probe solenoid isolates the probe and the exudate bottle for pressure testing via the first pressure sensor and the second pressure sensor to ensure that a seal is present between the probe and the wound area; and
wherein the thermoelectric element absorbs excess heat from the ultra-violet light-emitting diode array and transfers the excess heat to an exhaust thereby optimizing the ultra-violet light emitting diode array.

2. The wound care system of claim 1, wherein the pump operates in at least one of a high vacuum state and a low vacuum state.

3. The wound care system of claim 1, comprising:
a pump solenoid fluidly coupled to the pump and electrically coupled to the processor; and
a vent solenoid fluidly coupled to the pump and electrically coupled to the processor.

4. The wound care system of claim 3, wherein vacuum pressure is applied to the wound area via selective actuation of the pump solenoid, the probe solenoid, and the vent solenoid.

5. The wound care system of claim 1, wherein the ultra-violet light-emitting diode array comprises at least one first diode and at least one second diode.

6. The wound care system of claim 5, wherein the at least one first diode emits UV-A light and the at least one second diode emits UV-C light.

7. The wound care system of claim 6, wherein the at least one second diode emits UV-C light for a duration of approximately three minutes per approximately 12 hours.

8. The wound care system of claim 1, wherein the probe is at least one of a patch probe, a spot probe, and a point probe.

9. The wound care system of claim 1, comprising:
a UV interlock optically coupled to the ultra-violet light-emitting diode array and electrically coupled to the processor; and
wherein the UV interlock deactivates the ultra-violet light-emitting diode array upon disconnection of the probe.

10. A method for treating a wound area, the method comprising:
coupling a probe to a control unit via a control fiber port;
applying the probe to a wound area;
generating ultra-violet light via an ultra-violet light-emitting diode array;
providing the ultra-violet light to the wound area via the probe;
cooling the ultra-violet light-emitting diode array via a thermoelectric element that is thermally exposed to the light-emitting diode array;
applying vacuum pressure to the wound area via a pump;
isolating the probe from the pump via a probe solenoid disposed between the pump and an exudate bottle; and
pressure testing the probe to ensure that a seal is present between the probe and the wound area via a first pressure sensor disposed between the pump and the probe solenoid and a second pressure sensor disposed between the probe solenoid and the exudate bottle.

11. The method of claim 10, wherein the applying vacuum pressure comprises selective actuation of a probe solenoid, a vent solenoid, and the pump solenoid.

12. The method of claim 10, wherein the applying vacuum pressure comprises:
applying a first vacuum pressure to the wound area for a first period of time; and
applying a second vacuum pressure to the wound area for a second period of time.

13. The method of claim 12, wherein the first period of time includes a range of approximately 24 to approximately 48 hours following a surgery.

14. The method of claim 12, wherein the second period of time follows the first period of time.

15. The method of claim 12, wherein the first vacuum pressure is greater than the second vacuum pressure.

16. The method of claim 10 wherein the generating ultra-violet light comprises:
generating UV-A light via at least one first diode; and
generating UV-C light via at least one second diode.

17. The method of claim 16, wherein the UV-C light is generated for a duration of approximately 3 minutes every 12 hours.

18. The method of claim 10, wherein the applying a probe comprises applying at least one of a patch probe, a spot probe, and a point probe.

* * * * *